United States Patent [19]

Yang

[11] Patent Number: 5,164,462
[45] Date of Patent: Nov. 17, 1992

[54] ULTRAVIOLET LIGHT ABSORBING COMPOUNDS AND SILICONE COMPOSITIONS

[75] Inventor: Shih-Liang S. Yang, San Gabriel, Calif.

[73] Assignee: Allergan, Inc., Irvine, Calif.

[21] Appl. No.: 691,149

[22] Filed: Apr. 25, 1991

[51] Int. Cl.$^5$ .......... C07F 7/10; C07F 7/18; C08G 77/388; G02B 1/04
[52] U.S. Cl. .......... 525/478; 351/160 R; 351/163; 523/107; 523/108; 525/477; 548/110
[58] Field of Search .......... 526/259; 523/107, 108; 351/160 R, 163; 524/91; 548/110; 525/477, 478

[56] References Cited

U.S. PATENT DOCUMENTS

| Re. 33,477 | 12/1990 | Loshaek | 351/160 |
|---|---|---|---|
| 4,250,268 | 2/1981 | Rody et al. | |
| 4,316,033 | 2/1982 | Ching | 524/91 |
| 4,380,643 | 4/1983 | Yoshida et al. | |
| 4,528,311 | 7/1985 | Beard et al. | |
| 4,555,545 | 11/1985 | Kimura et al. | |
| 4,608,050 | 8/1986 | Wright et al. | |
| 4,612,358 | 9/1986 | Besecke et al. | |
| 4,803,254 | 2/1989 | Dunks et al. | 525/477 |
| 4,868,251 | 9/1989 | Reich et al. | |
| 4,872,877 | 10/1989 | Tiffany | 351/160 R |
| 4,960,898 | 10/1990 | Sakuta et al. | 548/110 |
| 5,102,707 | 4/1992 | Canivenc et al. | 548/110 |

FOREIGN PATENT DOCUMENTS 0282294 9/1988 European Pat. Off.
2-051542 2/1990 Japan.

OTHER PUBLICATIONS

*Contact Lenses, A Clinical Approach to Fitting,* Robert H. Hales, 59, 199-204 (1978).

*Contact Lens Handbook,* James R. Lee, 5, 28-32, 70, 71, 117.

Primary Examiner—Veronica P. Hoke
Attorney, Agent, or Firm—Frank J. Uxa, Jr.; Gordon L. Peterson

[57] ABSTRACT

An ultraviolet light absorbing silicone composition comprising silicone base polymer and ultraviolet light absorbing component present as, or derived from, one or more ultraviolet light absorbing compounds having the following structure:

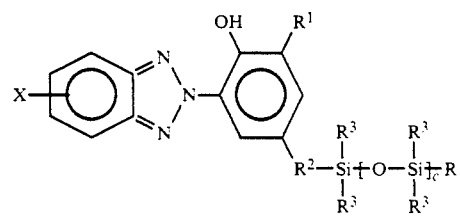

and mixtures thereof, wherein X is selected from the group consisting of H, alkoxy radicals and halogen; $R^1$ is selected from the group consisting of H and alkyl radicals, provided that at least one of X and $R^1$ is other than H; $R^2$ is selected from the group consisting of divalent hydrocarbon radicals, divalent substituted hydrocarbon radicals, oxo, divalent oxyhydrocarbon radicals and divalent substituted oxyhydrocarbon radicals; each $R^3$ is independently selected from the group consisting of alkyl radicals, substituted alkyl radicals, alkoxy radicals, substituted alkoxy radicals, aryl radicals, substituted aryl radicals and fluoro radical; R is selected from $R^3$, H and $CH=CH_2$, and c is an integer in the range of 1 to about 20.

22 Claims, No Drawings

5,164,462

1

ULTRAVIOLET LIGHT ABSORBING COMPOUNDS AND SILICONE COMPOSITIONS

BACKGROUND OF THE INVENTION

This invention relates to ultraviolet (UV) light absorbing compounds and polymer compositions, and more particularly, to UV light absorbing compounds and to polymer compositions including silicone polymers which compositions include, or are partially derived from, such UV light absorbing compounds. The subject polymer compositions, which are preferably optically clear, may be used in the fabrication of UV light absorbing ocular devices such as corneal contact lenses, intraocular lenses, and corneal intrastromal implant lenses.

The incident light entering the eye is composed of the entire spectrum of wavelengths including the ultraviolet, visible, and infrared. The cornea preferentially filters UV light in the range of about 300 nm to about 400 nm. Thus, in the eye with its natural lens in place relatively little radiation of wavelengths less that about 400 nm reaches the posterior intraocular structures, e.g., the vitreous humor and the retina.

In the aphakic individual, i.e., that individual who has had the natural crystalline lens removed, there is a loss in protection for the retina from UV light in the above-noted range. Thus., the use of UV light absorbing contact or intraocular lenses is particularly important for the aphakic person. It is further believed that UV light screening spectacles or contact lenses may retard the development of a cataract in the natural lens.

Although low molecular weight, non-polymerizable UV light absorbing compounds of various types are effective in blocking UV radiation when compounded into polymer formulations, their extractability in various media may limit their utility. Also, such UV light absorbing compounds have a potential for phase separation from the polymer formulation. This so-called "blooming" effect is dependent on how soluble the UV light absorbing compound is in the polymer. These problems are remedied by the synthesis of polymerizable, UV light absorbing monomers which can be covalently coupled into the polymer matrix. These covalently bonded UV light absorbing monomers are not extractable and do not phase separate from the remainder of the polymer. Articles fabricated from UV light absorbing silicone compositions incorporating these polymerizable UV light absorbing monomers therefore maintain stable ultraviolet screening characteristics and do not exhibit haze or blooming. The "blooming" problem could be solved by providing a UV light absorbing compound which, even though it is not polymerizable, has increased solubility in the polymer.

Reich, et al U.S. Pat. No. 4,868,251 discloses UV light absorbing compositions comprising silicone elastomers and, covalently bonded thereto, a UV light absorbing component derived from one or more of certain vinyl functional benzotriazole monomers. In preparing the final composition, heat and/or a co-solvent, such as isopropanol, is often needed to dissolve the UV light absorbing monomer in the silicone prepolymer. It would be advantageous to provide a UV light absorbing component which has substantial compatibility or solubility in the silicone prepolymers without requiring heat and/or a co-solvent. This would simplify, ease and quicken the manufacture of the final UV light absorbing polymeric composition. Further, an UV light absorbing component with enhanced compatibility and/or solubility would result in a monomer/prepolymer mix with a relatively long shelf life so that the mix could be produced and stored well before its ultimate use with little or no phase separation or other detrimental effect.

European Patent Publication No. 0282294 discloses vinylsilylalkoxy arylbenzotriazole monomers which are incorporated into optically clear silicone polymers. These silicon-containing monomers are taught as being more reactable with the silicone polymers than are non-silicon-containing monomers so that a more complete reaction and less non-reacted monomer are obtained. This publication still discloses the need for relatively high temperature, on the order of 90° C., to solubilize the monomer in the silicone prepolymer. Because of these elevated temperatures, the monomer is often mixed with only one portion or part of a conventional two part silicone formulation. The resulting additional mixing step adds to the cost and complexity of the final polymeric composition manufacturing process. Also, the limited solubility of this monomer reduces the effective shelf life of the prepolymer/monomer mixture.

Clearly, it would be advantageous to provide a new, preferably more soluble, class of UV light absorbing compounds, particularly for use in silicone polymers.

SUMMARY OF THE INVENTION

New UV light absorbing compositions and compounds have been discovered. The present compounds have excellent UV light absorbing properties and may be used in a variety of materials to provide desired UV light absorbance. These compounds are particularly useful for incorporation in the present compositions. The present compositions comprise silicone elastomer and UV light absorbing component present as, or derived from, one or more of certain UV light absorbing compounds. The present UV light absorbing compounds are readily soluble in the silicone prepolymer or prepolymers often without heating and/or the use of a co-solvent. Additionally, mixtures of the present UV light absorbing compounds and silicone prepolymers remain stable, for example, substantially homogenous, over long periods of time, i.e., have long shelf lives, even at temperatures of less than about 0° C. These features enhance the ease of manufacturing ocular products, such as lenses, from the present compositions. Mixtures of the UV light absorbing compound/silicone prepolymer/cross-linking agent are useful, for example, for producing solid, cured or cross-linked lens structures for the eye. The present compositions can be used to absorb radiation in the wavelength range of about 300 nm to about 400 nm. These compositions are preferably optically clear and can be utilized for the manufacture of corneal contact, intraocular and corneal intrastromal lenses. There is no significant phase separation, and preferably no significant extraction, of the UV light absorbing component, for example, during normal use of the compositions or lenses.

In one embodiment, the present UV light absorbing compounds comprise UV light absorbing benzotriazole derivatives having the following structure or formula:

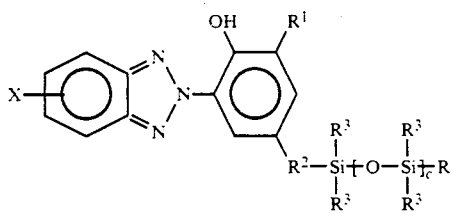

and mixtures thereof, wherein X is selected from the group consisting of H, alkoxy radicals, preferably containing 1 to about 6 carbon atoms, and halogen; $R^1$ is selected from the group consisting of H and alkyl radicals, preferably containing 1 to about 8, more preferably 1 to about 4, carbon atoms, provided that at least one of X and $R^1$ is other than H; $R^2$ is selected from divalent hydrocarbon radicals, such as alkylene radicals, divalent substituted hydrocarbon radicals, oxo, divalent oxyhydrocarbon radicals and divalent substituted oxyhydrocarbon radicals, preferably containing up to about 6 carbon atoms and more preferably containing 1 to about 4 carbon atoms, and still more preferably being an alkylene radical containing 1 to about 4 carbon atoms; each $R^3$ is independently selected from alkyl radicals, substituted alkyl radicals, alkoxy radicals, substituted alkoxy radicals, aryl radicals, substituted aryl radicals, and fluoro radical, preferably alkyl radicals, alkoxy radicals and aryl radicals and more preferably alkyl radicals and aryl radicals; R is selected from $R_3$, H and $CH=CH_2$; and c is an integer in the range of 1 to about 20, preferably 1 to about 4. In one particularly useful embodiment, where the UV light absorbing compound is polymerizable, R is selected from H and $CH=CH_2$.

The UV light absorbing compositions of the present invention are preferably optically clear, stable materials useful in the fabrication of corneal contact lenses, corneal intrastromal lenses and intraocular lenses. About 0.05% or 0.1% to about 5% by weight of the UV light absorbing component is preferably included in the composition to yield the appropriate UV light blocking efficiency, e.g., in samples of thickness comparable to the final lens products. For example, the UV light absorbing compositions of the present invention can be formulated to completely block ultraviolet radiation in the range of about 300 nm to about 390 nm and to display about 2% to about 20% transmittance at 400 nm for 0.75 mm thick samples.

The UV light absorbing silicone polymeric compositions substantially retain the physical characteristics of the non-UV light absorbing silicone polymeric compositions. The silicone compositions are such that the UV light absorbing component may be covalently attached thereto. Suitable silicone elastomers include, for example, two part platinum catalyzed, vinyl/hydride, addition cured polysiloxanes, such as polydimethylsiloxanes, poly dimethyl-diphenyl siloxanes, and polyorganofluorosiloxanes, as well as other addition cured polyorganosiloxanes and the like and mixtures thereof.

The present polymerizable or functional UV light absorbing compounds or monomers are preferably reacted with hydride or vinyl functional siloxane prepolymers and/or with hydride or vinyl functional cross-linking or cross-linker agents or components to covalently attach the UV light absorbing component. The cross-linking components are preferably components of a two-part platinum catalyzed, addition cured silicone elastomer formulation. The UV light absorbing component is preferably attached to the prepolymer and/or to a siloxane cross-linking component by a platinum catalyzed reaction. For example, the UV light absorbing monomer may act to form a bridging group similar to that which forms when the siloxane cross-linking component reacts with the siloxane prepolymer in the normal curing process to form the silicone elastomer.

DETAILED DESCRIPTION OF THE INVENTION

The present invention relates to an ultraviolet light absorbing composition comprising a silicone elastomer and an effective amount of UV light absorbing component, which may be physically mixed with and/or covalently bonded to (and a part of) the silicone elastomer.

The present UV light absorbing compounds, for example, which are the UV light absorbing components of the present compositions, or from which the UV light absorbing components of the present compositions are derived, comprise one or more UV light absorbing benzotriazole compounds having the following structure or formula:

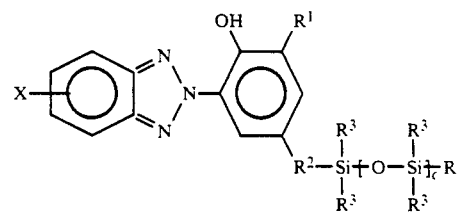

and mixtures thereof, wherein X is selected from the group consisting of H, alkoxy radicals, preferably containing 1 to about 6 carbon atoms, and halogen; $R^1$ is selected from the group consisting of H and alkyl radicals, preferably containing 1 to about 8, more preferably 1 to about 4 carbon atoms, provided that at least one of X and $R^1$ is other than H; $R^2$ is selected from divalent hydrocarbon radicals such as alkylene radicals, divalent substituted hydrocarbon radicals, oxo, divalent oxyhydrocarbon radicals and divalent substituted oxyhydrocarbon radicals, preferably containing up to about 6 carbon atoms and more preferably containing 1 to about 4 carbon atoms, and still more preferably being an alkylene radical containing 1 to about 4 carbon atoms; each $R^3$ is independently selected from alkyl radicals, substituted alkyl radicals, alkoxy radicals, substituted alkoxy radicals, aryl radicals, substituted aryl radicals, and fluoro radical, preferably from alkyl radicals, alkoxy radicals and aryl radicals and more preferably from alkyl radicals and aryl radicals; R is selected from $R^3$, H and $CH=CH_2$; and c is an integer in the range of 1 to about 10, preferably 1 to about 4. One or more of the $R^3$s may be organo fluoro radicals, for example, fluoro hydrocarbon radicals. In the event the UV light absorbing compound is polymerizable, R is selected from H and $CH=CH_2$.

In the event that any $R^3$ is aliphatic, it preferably contains 1 to about 8, more preferably 1 to about 4, carbon atoms. If any $R^3$ is aromatic, it preferably contains 6 to about 10, and more preferably 6, carbon atoms. In a particularly useful embodiment, each $R^3$ is independently selected from methyl radicals, substituted methyl radicals, phenyl radicals and substituted phenyl radicals. In the event that $R^1$ is alkyl, it is preferably tertiary alkyl, and more preferably t-butyl.

Examples of useful alkoxy radicals include methoxy, ethoxy, propoxy, butoxy, hexoxy and the like. A particularly useful halogen group for use as x is chloro. Examples of useful alkyl groups include methyl, ethyl, propyl, butyl, hexyl, octyl and the like. Examples of useful alkylene groups include ethylene, propylene, butylene and the like. Examples of useful aryl radicals include phenyl, methyl phenyl, ethyl phenyl, dimethyl phenyl and the like. The substituted groups referred to herein are exemplified by the above-noted groups (and the other groups referred to herein) substituted with one or more substituent groups including elements such as oxygen, nitrogen, carbon, hydrogen, halogen, sulfur, phosphorus and the like and mixtures or combinations thereof.

A particularly useful class of UV light absorbing compounds is selected from compounds having the following formula or structure

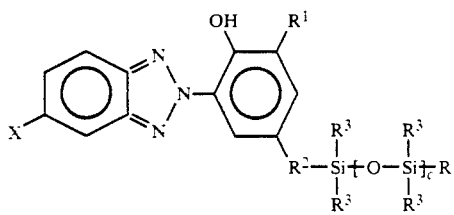

All tautomers, isomers and the like and mixtures thereof of the present UV light absorbing compounds are included within the scope of the present invention. For example, if $R^2$ is an ethylene radical, it may be bonded to the aromatic ring at either the alpha carbon atom or the beta carbon atom. Also, a mixture of such alpha and beta isomers may be used and is included in the scope of the present invention.

The present hydride functional UV light absorbing compounds can be prepared, for example, using the vinyl functional, benzotriazole derivatives disclosed in Reich et al U.S. Pat. No. 4,868,251 as starting materials. Such vinyl functional, benzotriazole derivative is reacted with a siloxane having at least two functional hydride groups if the UV light absorbing compound is to be polymerizable or with a siloxane having only one functional hydride group if a non-polymerizable UV light absorbing compound is to be produced. This reaction preferably occurs in the liquid phase, using a conventional solvent such as toluene, in the presence of a catalyst, such as a platinum-containing catalyst. Reaction conditions are sufficient to allow the vinyl group of the benzotriazole derivative to react with one of the hydride groups (or the only functional hydride group) of the siloxane. Such conditions can include a temperature in the range of about $-60°$ C. to about $50°$ C. and reaction times in the range of about 1 hour or less to about 60 hours or more. The resulting hydride functional UV light absorbing monomer or monomers or non-polymerizable UV light absorbing compound or compounds can be recovered, separated and/or purified using conventional techniques, such as distillation, extraction and the like.

The present hydride functional UV light absorbing monomers can be used to prepare the present vinyl functional UV light absorbing monomers. Thus, such hydride functional monomers can be reacted with acetylene to form the present vinyl functional monomers. This reaction preferably occurs in the liquid phase, using a conventional solvent such as toluene, in the presence of a catalyst, such as a platinum-containing catalyst. Reaction conditions are sufficient to allow the hydride group of the hydride functional monomer to react with the acetylene. Such conditions can include a temperature in the range of about $-60°$ C. to about $50°$ C. and reaction times in the range of about 0.2 hours or less to about 10 hours or more. The resulting vinyl functional UV light absorbing monomer or monomers can be recovered, separated and/or purified using conventional techniques, such as distillation, extraction and the like.

In accordance with one aspect of this invention, new compositions of matter comprising one or more UV light absorbing silicone elastomers, for example, UV light absorbing polysiloxanes, preferably polyorganosiloxane elastomers, are provided. These compositions are prepared by the incorporation of certain UV light absorbing compounds, for example, by the covalent attachment of certain polymerizable UV light absorbing monomers, as described herein, to silicone materials, preferably to hydride or vinyl functional siloxane base polymers (or pre-polymers) and cross-linking agents or components. The present compositions preferably further comprise at least one reinforcing agent, such as reinforcing silicone resins, silica and the like which are conventionally used to strengthen silicone elastomeric compositions. The reinforcing agent or agents are present, if at all, in an amount effective to enhance the strength of the composition relative to a substantially identical composition without such agent or agents. For example, the reinforcing agent or agents may be present in an amount up to about 50% by weight or more based on the silicone elastomer present in the composition. In one embodiment, the base polymers utilized in the present invention have the following structure or formulation:

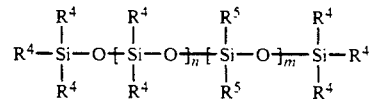

and mixtures thereof, wherein each $R^4$ and $R^5$ is independently selected from the group consisting of H, $CH=CH_2$, alkyl radicals, substituted alkyl radicals, alkoxy radicals, substituted alkoxy radicals, alkenyl radicals with a terminal double bond, substituted alkenyl radicals with a terminal double bond, aryl radicals, substituted aryl radicals and fluoro radical, provided that at least one, and preferably at least two, of the $R^4$s is selected from H and olefinically unsaturated groups; and n and m each is an integer independently selected from integers in the range of 0 to about 20,000. In the event that one or more $R^4$s and/or $R^5$s are fluoro radicals, one or more other $R^4$s and/or $R^5$s are preferably organic radicals. One or more of the $R^4$s and/or $R^5$s may be organo fluoro radicals, for example, fluoro hydrocarbon radicals. In one embodiment, each of the $R^4$s, other than those which are selected from H and olifinically unsaturated groups, and the $R^5$s is methyl. Each of the $R^4$s and $R^5$s may be independently selected from alkyl radicals containing 1 to about 4 carbon atoms, fluoro alkyl radicals containing 1 to about 3 carbon atoms, phenyl radicals, substituted aryl radicals, alkenyl radicals containing 2 to about 4 carbon atoms and having a terminal double bond and mixtures thereof.

Examples of useful alkenyl groups include ethenyl, propenyl, butenyl, hexenyl, octenyl and the like.

The cross-linking or cross-linker agents useful in the present invention are preferably components of a two part, silicone elastomer formulation, more preferably a two part, platinum catalyzed vinyl/hydride, addition cured silicone elastomer formulation. In one embodiment, the attachment of the UV light absorbing monomer to the silicone elastomer preferably proceeds by a platinum catalyzed reaction to form an ethylenic bridging group similar to that which forms when a cross-linking molecule binds together siloxane base polymer molecules in the normal curing or cross-linking reaction of the silicone elastomer. Thus, when the base polymer is vinyl functional, the UV light absorbing monomer can be either vinyl functional or hydride functional, preferably vinyl functional, and the cross-linking agent is hydride functional. Conversely, when the base polymer is hydride functional, the UV light absorbing monomer can be either vinyl functional or hydride functional, preferably hydride functional, and the cross-linking agent is vinyl functional. In addition, one or more of the base polymer and the cross-linking agent can be both vinyl and hydride functional.

In any event, the silicone elastomer is cross-linked and optically clear, and includes an effective UV light absorbing amount of the UV light absorbing component of the present invention physically mixed and/or covalently bonded within the silicone elastomer. These optically clear, UV light absorbing elastomeric compositions are very effective for inclusion in corneal contact lenses, intraocular lenses and corneal intrastromal lenses. Conventional lens forming techniques, for example, molding techniques, can be used to provide lenses comprising the present UV light absorbing elastomeric compositions.

The preferred siloxane cross-linking agents include a plurality, in particular at least three (3) of functional groups per molecule. Thus, each cross-linking molecule preferably can participate both in the covalent attachment of the UV absorbing monomer as well as in the formation of cross-links between siloxane base polymer molecules.

Suitable cross-linking agents include agents which are conventionally used to produce cross-linked silicone polymers, in particular, polysiloxane elastomers, for example, employing two part platinum catalyzed silicone systems to produce silicone elastomers by vinyl/hydride addition curing. Thus, suitable cross-linking agents are available as a component of many such conventional two part systems. Specific examples of effective cross-linking agents include 1,3,5,7-tetramethylcyclotetrasiloxane, methyl hydropolysiloxane, 1,3,5-trivinyl-1,1,3,5,5-pentamethyl-trisiloxane, methyl vinyl polysiloxane and the like.

The relative amounts of base polymer, UV light absorbing compound and cross-linking agent employed to produce the final composition, e.g., the siloxane elastomer composition, are chosen to provide a final composition having the desired properties, including the desired degree of cross-linking and the desired degree of UV light absorbing ability. The relative amounts of the components utilized varies depending on many factors, for example, on the specific components being employed, and on the application for which the final composition is to be employed. As noted above, conventional two part silicone polymer formulations can be employed. Any adjustments to these conventional formulations (in terms of relative amounts of components) are relatively minor (if required at all) to insure that the relatively minor amount of UV absorbing monomer is effectively incorporated, e.g., physically mixed and/or covalently attached, within the final composition.

The incorporation of the UV light absorbing compound can be made to occur at one or more of various steps in the process of producing an UV light absorbing silicone elastomer. One method is to simply dissolve the UV light absorbing compound into a mixture of the silicone components and to allow the incorporation of the UV light absorbing monomer to occur simultaneous to the formation of the base polymer cross-links. The UV light absorbing compound can be combined with the silicone components just prior to the polymerization reaction, for example, at the mixing or injection head. Also, if desired, the UV absorbing compound can be combined with all or a portion of the silicone components to be polymerized to form a homogeneous mixture which is stored, for example, for relatively long periods of time, on the order of days or weeks, preferably at reduced temperatures, for example about $-80°$ C. to about $0°$ C., before the polymerization reaction. The present benzotriazole-type UV light absorbing compounds have sufficient solubility so that 1% by weight of a benzotriazole-type UV light absorbing compound in accordance with the present invention remains in solution in a curable liquid mixture including all the precursor components of a platinum-catlayzed, cross-linked silicone elastomer even after such mixture is maintained for one week at $-60°$ C. This unique solubility feature allows silicone compositions to be prepared and stored well in advance of the final polymerization/curing without phase separation or precipitation of the UV light absorbing compound, and without uneven or premature curing of the mixture. Alternatively, the presently polymerizable UV light absorbing monomer can be pre-reacted with the cross-linking agent to form essentially a UV light absorbing, cross-linking adduct. The composite molecule is subsequently formulated with siloxane base polymer, and preferably additional platinum catalyst, to be cured into the UV light absorbing silicone elastomer. In any case a degree of incorporation of the UV light absorbing compound of greater that 95% is preferably obtained.

The UV light absorbing component covalently attached within the silicone elastomer does not leach out in aqueous or organic solvents, for example isopropanol.

The present UV light absorbing compound often absorb ultraviolet light strongly in the range of about 300 nm to about 400 nm, and exhibit reduced absorption at wavelengths higher that about 400 nm.

Preferably, the maximum amount of the UV light absorbing compound incorporated in the UV light absorbing composition of the present invention is about 5% by weight. More preferably, the UV light absorbing compound is incorporated into the UV light absorbing composition in an amount in the range of about 0.05% to about 5% by weight and still more preferably about 1% or less by weight, especially about 0.1% to about 1% by weight, based on the total composition. Of course, it is understood that the present polymerizable UV absorbing monomer is not present as such in the composition, but is part of the polymer. However, for convenience and simplicity, in certain instances herein the UV light absorbing monomer is referred to as being present in the polymer. The percentage of UV light absorbing monomer in the polymer referred to herein means the weight percent of such monomer based on the total material included in the composition. The amount of UV light absorbing compound included is that required to give the degree of light absorption desired and is dependent, for example, on the specific UV light absorbing compound or compounds employed, the specific silicone elastomer producing monomer or monomers employed and on the thickness, e.g., the optical path, of the product, e.g., lens, to be made from the polymeric composition. By Beers Law of Absorption, the required amount of absorber is inversely proportional to the optical path length through the lens device. It is often desired that the ultraviolet light transmission at 400 nm be less than about 10 to 15% of the incident light and at 390 nm be less than about 3%. The visible light transmission in the 410–450 nm range often should not be reduced below about 50% of the total light.

As noted above, the present UV light absorbing compounds have substantial compatibility with, e.g., solubility in, the base polymers or prepolymers and/or other silicone, in particular siloxane, molecules (e.g., cross-linking agents) used in producing the final silicone elastomer. Thus, in many instances the UV light absorbing compounds can be dissolved in the prepolymer/compound mix without using a co-solvent and/or without the application of heat. In one embodiment, the present invention involves benzotriazole derivatives effective to absorb, preferably preferentially absorb, UV light and having melting points less than 25° C. Since a uniform mixture can often be prepared at room temperature, that is on the order of about 20° C. to about 25° C., such mixture can be very conveniently prepared, e.g., at room temperature, without concern for premature and uneven curing, since curing often occurs at relatively elevated temperatures.

The present UV light absorbing compounds can be used very effectively as a component of a curable liquid composition comprising, in addition to the UV light absorbing compound, a cross-linkable siloxane base polymer or prepolymer, a cross-linking agent, e.g., as described herein, and a cross-linking catalyst, such as a platinum-containing catalyst as described herein. Such curable liquid composition can be stored at reduced temperature, for example, about −80° C. to about 0° C. for long, on the order of days or weeks, or even indefinite periods of time without concern for precipitation or phase separation of the UV light absorbing compound, or for uneven or premature curing. The curable liquid composition can be injected into the lens capsule of the eye where it is cured at body temperature to a solid, transparent lens which has effective UV light absorbing properties. The use of curable liquid compositions to produce lens structures is disclosed in Wright et al U.S. Pat. No. 4,608,050, which is incorporated in its entirety herein by reference.

The invention will be further described in connection with the following examples which are set forth for purposes of illustration only.

The starting material in Example 1 is 2-(2'-hydroxy-3'-t-butyl-5'-vinylphenyl)-5-chloro-2identified as "I", which itself can be produced as described in Reich et al U.S. Pat. No. 4,868,251, which is incorporated in its entirety herein by reference.

EXAMPLE 1

Preparation of
2-[3'-t-butyl-2'-hydroxy-5'-(2''-(7'''-hydro octamethyl tetrasiloxane)ethyl) phenyl]-5-chloro-2H-benzotriazole
and 2-[3'-t-butyl-2'-hydroxy-5octamethyl tetrasiloxane)ethyl) phenyl]-5-chloro-2H-benzotriazole mixture The above-noted mixture of the present UV light absorbing monomers is prepared to be used in preparing the mixture of UV light absorbing monomers in Example 2 and the UV light absorbing silicone composition of Example 4.

A 100 ml 3 neck flask equipped with a magnetic stirring bar, an inert gas inlet topped reflux condenser and a thermocouple was charged with 20 g (0.071 mole) 1,1,3,3,5,5,7,7-octamethyltetrasiloxane (from Petrarch Systems, Inc.), 4.0 g (0.012 mole) of I and 10 g dry toluene The mixture was stirred at room temperature for 1 hour until all of the I dissolved. 1 ml platinum complex solution (Petrarch Systems, Inc., catalog no. PC-075) was added and the reaction mixture was stirred at room temperature for 48 hours. Unreacted octamethyltetrasiloxane and toluene were removed by vacuum. 7.5 g (100%) yellow viscous oil, hereinafter identified as "II" was isolated Using conventional chromatography techniques, II can be further purified, if desired However, this yellow viscous oil, without further purification, is effective as a polymerizable UV light absorbing monomer mixture. This mixture remained as a liquid even at −60° C.

Mass spectroscopy analysis indicated a molecular weight for II of 610. High pressure liquid chromatography analysis showed essentially two components corresponding to the IIa (80%) and IIb (20%) isomers, shown below. The structures of IIa and IIb isomers and the corresponding concentration ratio were confirmed by UV/VIS, IR, and $^1$H NMR analyses.

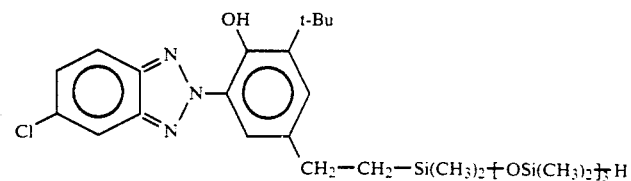

IIa

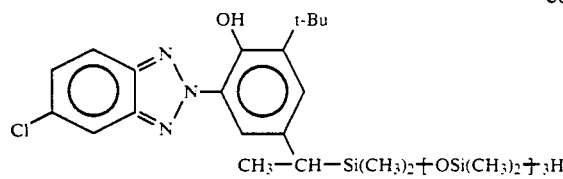

IIb

This mixture is found to have very effective UV light absorbing properties.

EXAMPLE 2

Preparation of a 2-[3'-t-butyl-2'-hydroxy-5'-(2'''-(7''''-vinyl octamethyl tetrasiloxane) ethyl) phenyl]-5-chloro-2H-benzotriazole and 2-[3'-t-butyl-2'-hydroxy-5'-(7''''-vinyl octamethyl tetrasiloxane) ethyl) phenyl]5-chloro-2H-benzotriazole mixture The above-noted mixture of the present UV light absorbing monomers is prepared to be used in preparing the UV light absorbing silicone composition of Example 3.

A 100 ml, 3 neck flask equipped with a magnetic stirring bar, a reflux condenser, an acetylene gas inlet, and a thermocouple was charged with 2 g of II (the mixture of isomers) and 60 ml dry toluene. The mixture was stirred at room temperature for 10 minutes until all II dissolved. The solution was purged with dry, scrubbed acetylene gas for 2 hours 1 ml platinum complex solution was added The reaction mixture was stirred and purged with acetylene continuously at room temperature for 6 hours. Unreacted acetylene and toluene were removed by vacuum. 2.0 g (100%) yellow viscous oil, hereinafter identified as "III", was isolated. Using conventional chromatography techniques, III can be further purified, if desired However, this isolated product is effective as a polymerizable UV light absorbing monomer mixture This mixture remained as a liquid even at −60° C.

Mass spectrometry analysis indicated a molecular weight for III of 636. High pressure liquid chromatography analysis showed two components corresponding to the IIIa (80%) and IIIb (20%) isomers, shown below The structures of the IIIa and IIIb isomers and the corresponding concentration ratio were confirmed by UV/VIS, IR, and ¹H NMR analyses

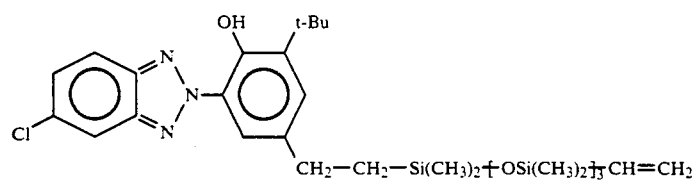

IIIa

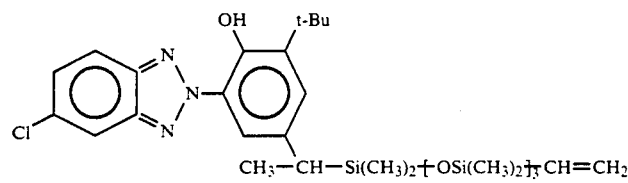

IIIb

This mixture is found to have very effective UV light absorbing properties.

EXAMPLE 3

Preparation of UV Absorbing Silicone

A glass beaker was charged with 10.20 g of part A, and 10.10 g of part B of a fast cure silicone RTV (McGhan Nusil Corporation Med-6230), and 0.066 g of III (the mixture of isomers). The contents were mixed thoroughly with a glass rod at room temperature. The resulting mixture was deaerated under vacuum and cured at 100° C. for 15 minutes in a mold into a 0.78 mm thick film. This film was extracted with toluene for 8 hours. Both the original film (pre-extraction), which included about 0.32% by weight of the UV light absorbing component, and the extracted film (post extraction) were optically clear and were tested for UV light absorbance.

Results of these tests are as follows:

| | % transmission | | | | | | |
|---|---|---|---|---|---|---|---|
| | 0.5% | 1.0% | 10% | 30% | 50% | 70% | 80% |
| UV light cutoff (nm) | | | | | | | |
| pre-extraction | 386 | 388 | 396 | 401 | 405 | 410 | 415 |
| post-extraction | 382 | 384 | 393 | 399 | 404 | 409 | 415 |

These results indicate that both the original film and the extracted film have very good UV light absorbing properties. Further, the extracted film showed no significant change in UV light absorbing properties relative to the film before extraction. The minor differences in the transmission profiles of the original and purified films may result from the use of an unpurified form of the UV light absorbing monomer and/or the presence of non-reacted, extractable silicones which are bonded to some of the UV light absorbing monomer and are lost during extraction.

EXAMPLE 4

Example 3 was repeated using a somewhat larger amount of II (the mixture of isomers) in place of III. Both the film before extraction, which included 0.54% by weight of the UV light absorbing component and the extracted film were optically clear and were tested for UV light absorbance.

Results of these tests were as follows:

| | % transmission | | | | | | |
|---|---|---|---|---|---|---|---|
| | 0.5% | 1.0% | 10% | 30% | 50% | 70% | 80% |
| UV light cutoff (nm) | | | | | | | |
| pre-extraction | 391 | 394 | 400 | 405 | 410 | 415 | 419 |
| post-extraction | 389 | 390 | 398 | 403 | 407 | 412 | 417 |

These results indicate that both the original film and properties. Further, the extracted film showed no significant change in UV light absorbing properties relative to the film before extraction.

EXAMPLE 5

Preparation of
2-[3'-t-butyl-2'-hydroxy-5'(2"-heptamethyl trisiloxane ethyl) phenyl]-5-chloro-2H-benzotriazole and
2-[3'-t-butyl-2'-hydroxy-5'-(1"-heptamethyltrisiloxane ethyl) phenyl]-5-chloro-2H-benzotriazole mixture A 100 ml 3 neck flask equipped with a magnetic stirring bar, an inert gas inlet topped reflux condenser and a thermocouple is charged with 20 g (0.09 mole) 1,1,1,3,3,5,5-heptamethyltrisiloxane (Petrarch Systems, Inc.), 4.0 g (0.012 mole) of I and 10 g dry toluene. The mixture is stirred at room temperature for 1 hr until all I dissolved. 1 ml platinum complex solution (Petrarch Systems, Inc., catalog no. PC-075) is added and the reaction mixture is stirred at room temperature for 48 hrs. Unreacted heptamethyltrisiloxane and toluene are removed by vacuum. A yellow viscous oil, hereinafter identified as IV, is isolated using conventional chromatography techniques, IV can be further purified, if desired. However, this yellow viscous oil, without further purification is effective as a UV light absorbing component. This oil remains a liquid even at −30° C.

Mass spectroscopy analysis indicates a molecular weight for IV of about 550. HPLC analysis shows essentially two components corresponding to the IVa and IVb isomers.

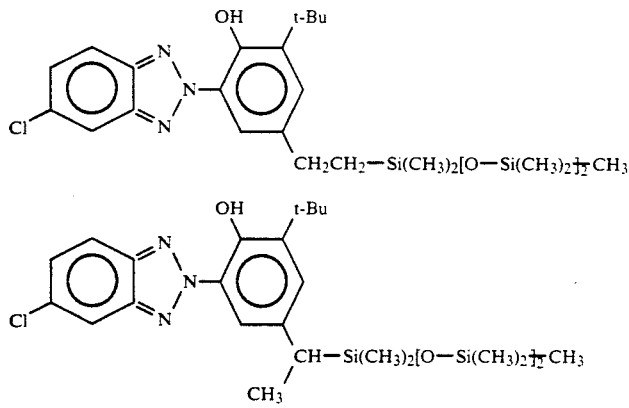

This mixture is found to have very effective UV light absorbing properties.

EXAMPLE 6

Example 3 is repeated using IV (the mixture of isomers) in place of III. The film is extracted with water, instead of toluene, for 8 hours. Both the film before extraction and the extracted film are optically clear and are tested for UV light absorbance and are found to have very good UV light absorbing properties.

While this invention has been described with respect to various specific examples and embodiments, it is to be understood that the invention is not limited thereto and that it can be variously practiced within the scope of the following claims.

What is claimed:

1. An ultraviolet light absorbing silicone composition comprising silicone elastomer and an effective amount of ultraviolet light absorbing component covalently bonded to said silicone elastomer and derived from one or more ultraviolet light absorbing compounds selected from the group consisting of compounds having the following structure

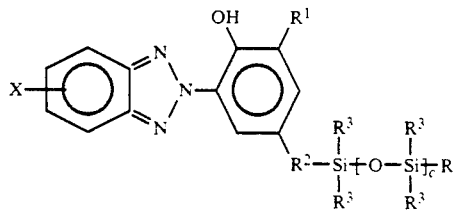

and mixtures thereof, wherein X is selected from the group consisting of H, alkoxy radicals and halogen; $R^1$ is selected from the group consisting of H and alkyl radicals, provided that at least one of X and $R^1$ is other than H; $R^2$ is selected from the group consisting of divalent hydrocarbon radicals, divalent substituted hydrocarbon radicals, oxo, divalent oxyhydrocarbon radicals and divalent substituted oxyhydrocarbon radicals; each $R^3$ is independently selected from the group consisting of alkyl radicals, substituted alkyl radicals, alkoxy radicals, substituted alkoxy radicals, aryl radicals, substituted aryl radicals and fluoro radical; R is selected from the group consisting of H and $CH=CH_2$; and c is an integer in the range of 1 to about 20.

2. The composition of claim 1 wherein each $R^3$ is independently selected from the group consisting of alkyl radicals and aryl radicals.

3. The composition of claim 1 wherein $R^1$ is selected from alkyl radicals.

4. The composition of claim 1 wherein said compounds have the following structure:

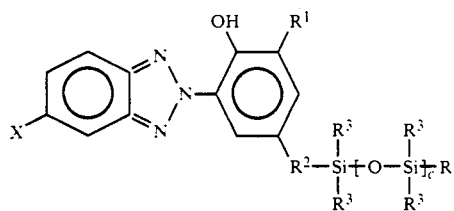

5. The composition of claim 1 wherein said silicone elastomer is a vinyl/hydride addition cured polysiloxane.

6. The composition of claim 1 wherein each R3 is independently selected from the group consisting of alkyl radicals having 1 to about 4 carbon atoms, substituted alkyl radicals having 1 to about 4 carbon atoms, alkoxy radicals having 1 to about 4 carbon atoms, substituted alkoxy radicals having 1 to about 4 carbon atoms, phenyl radicals and substituted phenyl radicals.

7. The composition of claim 1 wherein each $R^3$ is a methyl radical and c is an integer in the range of 1 to about 4.

8. The composition of claim 1 wherein $R^2$ is selected from the group consisting of methylene, substituted methylene, ethylene, substituted ethylene, oxo, divalent oxyhydrocarbon radicals, and divalent substituted oxyhydrocarbon radicals.

9. The composition of claim 1 wherein said ultraviolet light absorbing component is about 0.05% to about 5% by weight of said composition.

10. A corneal contact lens, an intraocular lens or a corneal intrastromal lens comprising the composition of claim 1, provided said composition is optically clear.

11. A composition curable into a cross-linked polymer composition comprising a cross-linkable siloxane polymer, a cross-linking component capable of reacting with said cross-linkable siloxane polymer, and at least one component capable of reacting with at least one of said cross-linkable siloxane polymer and said cross-linking component in an amount effective to render said cross-linked polymer composition ultraviolet light absorbing, said component having the following structure

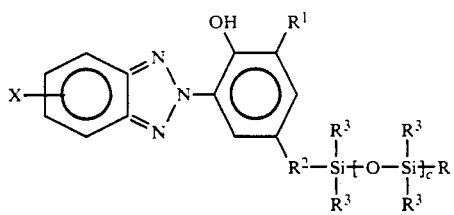

and mixtures thereof, wherein X is selected from the group consisting of H, alkoxy radicals and halogen, $R^1$ is selected from the group consisting of H and alkyl radicals, provided that at least one of X and $R^1$ is other than H, $R^2$ is selected from the group consisting of divalent hydrocarbon radicals, divalent substituted hydrocarbon radicals, oxo, divalent oxyhydrocarbon radicals and divalent substituted oxyhydrocarbon radicals, each $R^3$ is independently selected from the group consisting of alkyl radicals, substituted alkyl radicals, alkoxy radicals, substituted alkoxy radicals, aryl radicals, substituted aryl radicals and fluoro radical, R is selected from the group consisting of H and CH=CH₂, and c is an integer in the range of 1 to about 20.

12. The composition of claim 11 wherein $R^2$ is selected from the group consisting of methylene, substituted methylene, ethylene, substituted ethylene, oxo, divalent oxyhydrocarbon radicals, and divalent substituted oxyhydrocarbon radicals.

13. A compound having the following formula

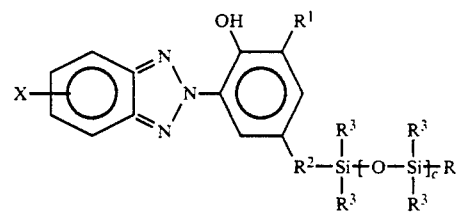

wherein X is selected from the group consisting of H, alkoxy radicals and halogen, $R^1$ is selected from the group consisting of H and alkyl radicals, provided that at least one of X and $R^1$ is other than H, $R^2$ is selected from the group consisting of divalent hydrocarbon radicals, divalent substituted hydrocarbon radicals, oxo, divalent oxyhydrocarbon radicals and divalent substituted oxyhydrocarbon radicals, each $R^3$ is independently selected from the group consisting of alkyl radicals, substituted alkyl radicals, alkoxy radicals, substituted alkoxy radicals, aryl radicals and substituted aryl radicals, R is selected from the group consisting of H and CH=CH₂, and c is an integer in the range of 1 to about 20.

14. The compound of claim 13 wherein each $R^3$ is independently selected from the group consisting of alkyl radicals and aryl radicals.

15. The compound of claim 13 wherein $R^1$ is selected from alkyl radicals.

16. The compound of claim 13 which has the following formula

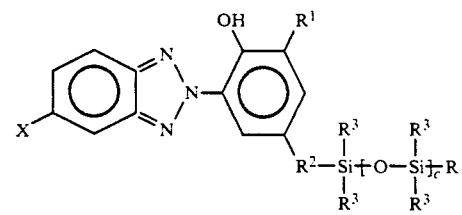

17. The compound of claim 13 wherein each $R^3$ is independently selected from the group consisting of alkyl radicals having 1 to about 4 carbon atoms, substituted alkyl radicals having 1 to about 4 carbon atoms, alkoxy radicals having 1 to about 4 carbon atoms, substituted alkoxy radicals having 1 to about 4 carbon atoms, phenyl radicals and substituted phenyl radicals.

18. The compound of claim 13 wherein each $R^3$ is a methyl radical and c is an integer in the range of 1 to about 4.

19. The compound of claim 13 wherein $R^2$ is an alkylene radical.

20. A compound or mixture of compounds selected from the group consisting of 2-[3'-t-butyl-2'-hydroxy-5'-(2"(7"'-vinyl octamethyl tetrasiloxane) ethyl) phenyl]-5-chloro-2H-benzotriazole, 2-[3'-t-butyl-2'hydroxy-5'octamethyl tetrasiloxane) ethyl) phenyl]5-chloro-2H-benzotriazole and mixtures thereof.

21. A compound having the following formula

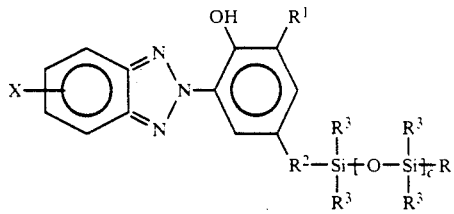

wherein X is selected from the group consisting of H, alkoxy radicals and halogen, $R^1$ is selected from the group consisting of alkyl radicals, $R^2$ is selected from the group consisting of divalent hydrocarbon radicals, divalent substituted hydrocarbon radicals, oxo, divalent oxyhydrocarbon radicals and divalent substituted oxyhydrocarbon radicals, each $R^3$ is independently selected from the group consisting of alkyl radicals, substituted alkyl radicals, alkoxy radicals, substituted alkoxy radicals, aryl radicals and substituted aryl radicals, R is selected from the group consisting of $R^3$, H and $CH=CH_2$, and c is an integer in the range of 1 to about 20.

22. A compound having the following formula

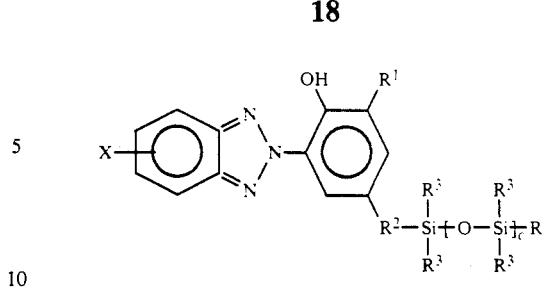

wherein X is selected from the group consisting of H, alkoxy radicals and halogen, $R^1$ is selected from the group consisting of H and alkyl radicals, provided that at least one of X and $R^1$ is other than H, $R^2$ is selected from the group consisting of methylene, substituted emthylene, ethylene, substituted ethylene, oxo, divalent oxyhydrocarbon radicals and divalent substituted oxyhydrocarbon radicals, each $R^3$ is independently selected from the group consisting of alkyl radicals, substituted alkyl radicals, alkoxy radicals, substituted alkoxy radicals, aryl radicals and substituted aryl radicals, R is selected from the group consisting of $R^3$, H and $CH=CH_2$, and c is an integer in the range of 1 to about 20.

* * * * *

UNITED STATES PATENT AND TRADEMARK OFFICE
CERTIFICATE OF CORRECTION

PATENT NO. : 5,164,462
DATED : November 17, 1992
INVENTOR(S) : Yang

It is certified that error appears in the above-identified patent and that said Letters Patent is hereby corrected as shown below:

Column 10, line 11; delete "2" and insert in place thereof -- 2H-benzotriazole, hereinafter --

Column 10, line 20; delete "5 octamethyl" and insert in place thereof -- 5'-(1''-7'''-hydro octamethyl --

Column 10, line 41; after "isolated" insert --,--

Column 10, lines 42-43; after "desired" insert --,--

Column 11, line 17; before "7'''-vinyl" insert -- (1'' - --

Column 11, line 37; after "desired" insert --,--

Column 11, line 39; after "mixture" insert --,--

Column 12, line 19; delete "100°C." and insert in place thereof --100°C--

Column 13, line 14; before "properties" insert -- the extracted film have very good UV light absorbing --

Column 15, line 15; delete "R3" and insert in place thereof --R³--

Column 16, line 64; add a space between "of" and "2"

Column 16, line 67; after "5" insert -- -(1''-(7'''-vinyl --

Signed and Sealed this

First Day of March, 1994

Attest:

BRUCE LEHMAN

Attesting Officer     Commissioner of Patents and Trademarks